United States Patent
Razavi et al.

(10) Patent No.: US 6,894,180 B2
(45) Date of Patent: May 17, 2005

(54) CATALYST STRUCTURE FOR OLEFIN POLYMERIZATION

(75) Inventors: Abbas Razavi, Mons (BE); Margarito Lopez, Pasadena, TX (US); Didier Baekelmans, Munich (DE); Vladimir Marin, Houston, TX (US)

(73) Assignee: Fina Technology, Inc., Houston, TX (US)

( * ) Notice: Subject to any disclaimer, the term of this patent is extended or adjusted under 35 U.S.C. 154(b) by 41 days.

(21) Appl. No.: 10/692,068

(22) Filed: Oct. 23, 2003

(65) Prior Publication Data

US 2004/0138055 A1 Jul. 15, 2004

Related U.S. Application Data

(63) Continuation-in-part of application No. 10/301,884, filed on Nov. 21, 2002, now abandoned.

(51) Int. Cl.$^7$ .............................. C07F 15/02; C08F 4/44; C08F 4/06; B01J 31/00; B01J 37/00
(52) U.S. Cl. .................. 556/35; 556/138; 502/103; 502/117; 502/167; 526/110; 526/161; 526/169; 526/172
(58) Field of Search ..................... 502/103, 117, 502/167; 556/35, 138; 526/110, 161, 169, 172

(56) References Cited

U.S. PATENT DOCUMENTS

| | | | |
|---|---|---|---|
| 4,665,208 A | 5/1987 | Welborn, Jr. et al. | |
| 4,874,734 A | 10/1989 | Kioka et al. | |
| 4,908,463 A | 3/1990 | Bottelberghe | |
| 4,924,018 A | 5/1990 | Bottelberghe | |
| 4,952,540 A | 8/1990 | Kioka et al. | |
| 4,968,827 A | 11/1990 | Davis | |
| 5,091,352 A | 2/1992 | Kioka et al. | |
| 5,103,031 A | 4/1992 | Smith, Jr. | |
| 5,145,819 A | 9/1992 | Winter et al. | |
| 5,158,920 A | 10/1992 | Razavi | |
| 5,198,401 A | 3/1993 | Turner et al. | |
| 5,204,419 A | 4/1993 | Tsutsui et al. | |
| 5,206,199 A | 4/1993 | Kioka et al. | |
| 5,235,081 A | 8/1993 | Sangokoya | |
| 5,243,001 A | 9/1993 | Winter et al. | |
| 5,248,801 A | 9/1993 | Sangokoya | |
| 5,308,815 A | 5/1994 | Sangokoya | |
| 5,643,847 A | 7/1997 | Waltzer, Jr. | |
| 6,002,033 A | 12/1999 | Razavi | |
| 6,066,588 A | 5/2000 | Razavi | |
| 6,143,686 A | 11/2000 | Vizzini | |
| 6,177,529 B1 | 1/2001 | Razavi et al. | |
| 6,194,343 B1 | 2/2001 | Collins et al. | |
| 6,211,110 B1 | 4/2001 | Santi et al. | |
| 6,228,795 B1 | 5/2001 | Vizzini | |
| 6,268,518 B1 | 7/2001 | Resconi et al. | |
| 6,313,243 B1 * | 11/2001 | Tohi et al. ................. 526/172 |
| 6,369,177 B1 * | 4/2002 | Tohi et al. ................. 526/172 |
| 6,743,932 B2 * | 6/2004 | Kristen et al. ............... 556/28 |
| 2004/0147389 A1 * | 7/2004 | Green et al. ................. 502/103 |

FOREIGN PATENT DOCUMENTS

| | | |
|---|---|---|
| EP | 0594218 | 9/1987 |
| EP | 0277003 | 8/1988 |
| EP | 0277004 | 8/1988 |
| EP | 0279586 | 8/1988 |
| EP | 0426637 | 10/1990 |
| EP | 0500944 | 7/1991 |
| EP | 0495375 | 1/1992 |
| EP | 0520732 | 6/1992 |
| EP | 0570982 | 5/1993 |
| EP | 0573403 | 6/1993 |
| EP | 0561476 | 9/1993 |
| WO | 9200333 | 1/1992 |
| WO | 9407928 | 4/1994 |
| WO | 9410180 | 5/1994 |
| WO | WO 99/65951 | * 12/1999 |
| WO | WO 99/65952 | * 12/1999 |

OTHER PUBLICATIONS

"The Search for New–Generation Olefin Polymerizatiojn Catalysts: Life Beyond Metallocenes," Agnew. Chem. Int. Ed. 1999, 38, 423–447.

Iron and Cobalt Ethylene Polymerization Catalysts Bearing 2,6–Bis(Imino) Pyridyl Ligands; Synthesis, Structures and Polymerization Studies, J. Am. Chem. Soc., 1999, 121, 8728–8740.

"Polymerization of Propylene by a New Generation of Iron Catalysts: Mechanisms of Chain Initiation, Propagation, and Termination," by Brook L. Small and Maurice Brookhart, *Macromolecules* 1999, 32, 2120–2130, 1999 American Chemical Society.

* cited by examiner

Primary Examiner—Mark L. Bell
Assistant Examiner—J. Pasterczyk
(74) Attorney, Agent, or Firm—Tenley R. Krueger

(57) ABSTRACT

A catalyst system having the following formula is described herein.

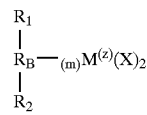

wherein M is a metal; each X is an atom or group banded to M and may be the same or different; $R_1$ and $R_2$ may be the same or each may be different and are substituted or unsubstituted cyclopentadienyl or aromatic groups; $R_B$ is a structural bridge between $R_1$ and $R_2$ imparting stereorigidity thereto and including at least one heteroatom bonded to M, with each of $R_1$ and $R_2$ bonded to the same or different heteroatom of $R_B$ which heteroatom is also bonded to M; Z is the coordination number of M and is greater than or equal to 4 and m is the number of bonds between M and heteroatoms of $R_B$.

8 Claims, No Drawings

CATALYST STRUCTURE FOR OLEFIN POLYMERIZATION

CROSS REFERENCE TO RELATED APPLICATIONS

This application is a continuation-in-part and claims priority from U.S. patent application Ser. No. 10/301,884 filed Nov. 21, 2002. Now abandoned.

BACKGROUND OF THE INVENTION

1. Field of the Invention

The present invention relates to catalyst components, catalyst systems, olefin polymerization, polymer compositions, and to articles made from such polymer compositions. More particularly the present invention relates to catalysts having $C_1$, $C_2$ or $C_S$ symmetry.

2. Description of the Related Art

As is well known, various processes and catalysts exist for the production of polyolefins. Traditional Ziegler-Natta catalyst systems utilize a transition metal compound cocatalyzed by an aluminum alkyl.

In the 1980's, metallocene catalysts for olefin polymerization were commercialized that included a metallocene and an aluminum alkyl component, with a transition metal compound having two or more cyclopentadienyl (Cp) ring ligands. Accordingly, titanocenes, zirconocenes and hafnocenes have all been utilized as the transition metal component in such a metallocene containing catalyst systems for the production of polyolefins. Metallocene catalysts can be cocatalyzed with an alumoxane, rather than an aluminum alkyl, to provide a metallocene catalyst system of high activity for the production of polyolefins.

In addition to Ziegler-Natta catalysts and metallocene catalysts, a number of "non-metallocene" type catalysts have been suggested for the polymerization of olefins. Specifically, for example, in *The Search for New-Generation Olefin Polymerization Catalysts: Life Beyond Metallocenes*, Angew. Chem. Int. Ed. 1999, 38, 428–447, Britovsek et al. review a number of olefin catalyst systems, including: Group 3 metal catalysts such as scandium and yttrium complexes; Rare Earth Metal catalysts such as lanthamide and actinide-based catalysts stabilized with substituted cyclopentadienyl ligands; cationic Group 4 metal complexes including carbon-based ligands (such as alkyl ligands, allyl ligands, Cp analogues), including nitrogen-based ligands (such as amide ligands either along or in combination with other ligands, amidinate ligands either alone or in combination with other ligands, and β-diketimate ligands), and including oxygen-based ligands (such as alkoxide ligands either alone or in combination with other ligands, bisalkoxides with additional donors); neutral Group 4 metal complexes; Group 5 metal catalysts; Group 6 metal catalysts; Group 8 metal catalysts; Group 9 metal catalysts; Group 10 metal catalysts; Group 13 metal catalysts.

Additionally, in *Iron and Cobalt Ethylene Polymerization Catalysts Bearing 2,6-Bis(Imino)Pyridyl Ligands; Synthesis, Structures, and Polymerization Studies*, J. Am. Chem. Soc. 1999, 121, 8728–8740, Britovsek et al. disclose certain iron and cobalt catalysts for the polymerization of ethylene.

WO 98/30612, published on Jul. 16, 1998, discloses selected iron complexes of 2,6-pyridinecarboxaldehydebis(imines) and 2,6-diacyclpyridinebis(imines) as catalysts for the polymerization of propylene. WO 99/12981, published on Mar. 18, 1999, discloses catalyst complexes having a bridge comprising heteroatoms bridging R groups $R^5$ and $R^7$, with these complexes taught as being useful "especially for polymerizing ethylene alone or for copolymerizing ethylene with higher 1-olefins" (page 2, lines 28–29). The bridged R groups $R^5$ and $R^7$ are independently selected from hydrogen, halogen, and hydrocarbyl, substituted hydrocarbyl, heterohydrocarbyl or substituted heterohydrocarbyl. There is no teaching or suggestion to make a chiral complex suitable for producing high tacticity, crystallinity polypropylene.

The following patents disclose bridged metallocene catalyst systems: U.S. Pat. No. 5,145,819, issued Sep. 8, 1992 to Winter et al.; U.S. Pat. No. 5,158,920, issued Oct. 27, 1992 to Razavi; U.S. Pat. No. 5,243,001, issued Sep. 7, 1993 to Winter et al.; U.S. Pat. No. 6,002,033, issued Dec. 14, 1999 to Razavi et al.; U.S. Pat. No. 6,066,588, issued May 23, 2000, to Razavi et al.; U.S. Pat. No. 6,177,529 B1, issued Jan. 23, 2001, to Razavi et al.; U.S. Pat. No. 6,194,343 B1, issued Feb. 27, 2001 to Collins et al.; U.S. Pat. No. 6,211,110 B1, issued Apr. 3, 2001 to Santi et al.; and U.S. Pat. No. 6,268,518 B1, issued Jul. 31, 2001 to Resconi et al.

However, in spite of the above advancements, there still exists a need in the art for catalyst compositions, methods of making such compositions, methods of polymerization using such compositions, to polymer compositions, and to articles made from such polymer compositions.

SUMMARY OF THE INVENTION

According to one embodiment of the present invention there is provided a bridged compound having the formula:

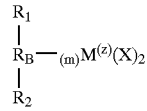

wherein M is a metal; each X is an atom or group covalently or ionically bonded to M and may be the same or different; $R_1$ and $R_2$ may be the same or each may be different and are substituted or unsubstituted cyclopentadienyl or aromatic rings; $R_B$ is a structural bridge between the cylcopentadienyl or aromatic rings $R_1$ and $R_2$ and imparts stereorigidity to the rings, and comprises at least one heteroatom bonded to M, with each of $R_1$ and $R_2$ bonded to the same or different heteroatom of $R_B$ which heteroatom is also bonded to M; Z is the coordination number of M and is greater than or equal to 4; m is the number of bonds between M and heteroatoms of $R_B$ and to impart stereorigidity m is equal or greater than 2; and with $R_1$, $R_2$ and $R_B$ selected to provide a catalyst component with $C_1$, $C_2$ or $C_S$ symmetry. The catalyst component can be chiral or non-chiral. In some embodiments it can be desirable to have the catalyst component that is chiral.

According to another embodiment of the present invention, there is provided a method of making a bridged metallocene compound comprising contacting a metal compound of the formula $M(X)_2$ with a bridged compound of the formula

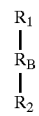

wherein $R_B$, $R_1$ and $R_2$ are as defined above.

According to another embodiment of the present invention, there is provided a catalyst system comprising an activated bridged metallocene compound having the formula:

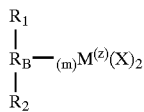

wherein M, X, $R_1$, $R_2$, m and Z are as defined above.

According to still another embodiment of the present invention, there is provided a method of making a catalyst system comprising contacting an activator with a bridged metallocene compound having the formula:

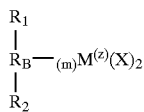

wherein M, X, $R_1$, $R_2$, m and Z are as defined above.

According to yet another embodiment of the present invention, there is provided a method of forming polyolefins comprising contacting olefin monomer or mixture of monomers in the presence of an activated bridged metallocene compound having the formula:

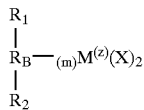

wherein M, X, $R_1$, $R_2$, m and Z are as defined above.

For all of the above embodiments, various further embodiments are provided by changing M, X, $R_1$, $R_2$, m and Z as described in the detailed description.

DETAILED DESCRIPTION OF THE INVENTION

In one embodiment of the invention a bridged metallocene catalyst component of the present invention can be represented by the following formula:

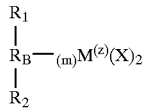

wherein M is a metal; each X is an atom or group covalently or ionically bonded to M and may be the same or different; $R_1$ and $R_2$ may be the same or each may be different and are substituted or unsubstituted cyclopentadienyl or aromatic rings; $R_B$ is a structural bridge between the cylcopentadienyl or aromatic rings $R_1$ and $R_2$ and imparts stereorigidity to the rings, and comprises at least one heteroatom bonded to M, with each of $R_1$ and $R_2$ bonded to the same or different heteroatom of $R_B$ which heteroatom is also bonded to M; Z is the coordination number of M and is greater than or equal to 4; m is the number of bonds between M and the heteroatom(s) of $R_B$ and to impart stereorigidity $m \geq 2$; because the number of bonds around M cannot exceed its coordination number Z; with $R_1$, $R_2$ and $R_B$ selected to provide a catalyst component with $C_1$, $C_2$ or $C_S$ symmetry.

The catalyst component can be chiral or non-chiral. In some embodiments it can be desirable to have the catalyst component that is chiral.

The metal M of the present invention may be any suitable metal useful as the metal component in metallocene catalysts. As a non-limiting example, M may be selected from among any metal as is known in the prior art to be useful as the metal component in metallocene catalysts. M will be selected to have a coordination number Z that is at least equal to the number of substituents bonded to M, that is, m number of $R_B$ heteroatom-to-metal bonds plus 2 (for both X's). M can be selected from among transition metals, lanthamides and actinides. M can be selected from among group 3d, 4d or 5d transition metals, such as Fe, Co, Ni, Ru, Rh, Pd, Os, Ir and Pt. In some embodiments M can be desirably selected from among Fe, Co and Ni. $R_1$ and $R_2$ may be the same or each may be different and may be generally described as being substituted or unsubstituted cyclopentadienyl or aromatic rings.

As non-limiting examples, $R_1$ and $R_2$ may be selected from among any substituted or unsubstituted cylcopentadienyl or aromatic ring as are known in the art to be useful in metallocene catalysts. Non-limiting examples of hydrocarbon radicals suitable for use as $R_1$ and $R_2$ are shown in the Examples below. As a nonlimiting example, $R_1$ and $R_2$ may be described as a cylcopentadienyl or aromatic ring of the form $(C_5(R')_4)$, wherein each R' may be the same or each may be different, and R' is a hydrogen or a substituted or unsubstituted hydrocarbyl radical having 1–20 carbon atoms.

Non-limiting examples of hydrocarbyl radicals suitable for use as R' include unsubstituted and substituted alkyl, alkenyl, aryl, alkylaryl or arylalkyl radicals. More specific non-limiting examples of suitable hydrocarbyl radicals include unsubstituted and substituted methyl, ethyl, propyl, butyl, amyl, isoamyl, hexyl, isobutyl, heptyl, octyl, nonyl, decyl, cetyl, phenyl, methylene, ethylene, propylene, and other like groups.

$R_B$ acts as a structural bridge between the cylcopentadienyl or aromatic rings $R_1$ and $R_2$ and imparts stereorigidity to the rings, and comprises n heteroatoms ("HA") bonded to M. The number of heteroatoms bonded to M can be $n \geq 1$, $n \geq 2$, and in some embodiments it can be desirable to have $n \geq 3$. An example of a suitable structural bridge $R_B$ is provided in the examples.

Heteroatoms useful in structural bridge $R_B$ include any that can be coordinated to the metal M by a "dative" bond, that is, a bond formed by the donation of a lone pair of electrons from the heteroatom. Where $R_B$ comprises more than one heteroatom bonded to M, they may be the same heteroatom or different heteroatoms. Non-limiting examples of suitable heteroatoms include O, N, S, and P. In some embodiments the heteroatoms are desirably N.

$R_1$ is bonded to a heteroatom of $R_B$ which heteroatom is also bonded to M, either directly or indirectly through a different heteroatom. Likewise, $R_2$ is also bonded to a heteroatom of $R_B$ which heteroatom is also bonded to M, either directly or indirectly through a different heteroatom. $R_1$ and $R_2$ may be bonded to the same heteroatom that is also bonded to M, or maybe bonded to different heteroatoms which different heteroatoms are also bonded to M. The structure of the R1—R2—$R_B$ moiety can be any that does not interfere with the symmetry of the catalysts. For example, the R1—R2—$R_B$ moiety can have the following configurations and still be within the scope of the claims of the present invention:

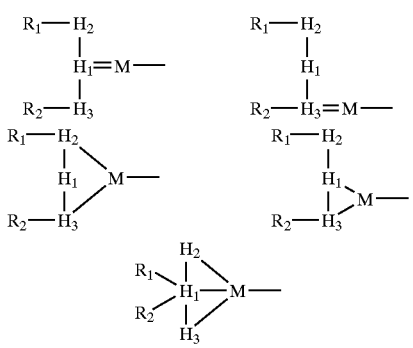

In some embodiments a bridging group having four heteroatoms would be within the scope of the present invention. According to one embodiment of the present invention, $R_1$, $R_2$ and $R_B$ are selected to provide a catalyst component that has $C_1$, $C_2$ or $C_S$ symmetry. Any configuration of $R_1$, $R_2$ and $R_B$ that does not disrupt the $C_1$, $C_2$ or $C_S$ symmetry known to those of ordinary skill in the art of preparing catalysts to be useful can be used with the present invention. The catalyst component can be chiral or non-chiral. In some embodiments it can be desirable to have a catalyst component that is chiral.

Each X may be an atom or group as are known to be utilized with catalysts, and is generally covalently or ionically bonded to M. Each X may be the same or different, although commonly each X is the same. As a non-limiting example, X may be selected from among halide, sulphate, nitrate, thiolate, thiocarboxylate, $BF_4^-$, $PF_6^-$, hydride, hydrocarbyloxide, carboxylate, substituted or unsubstituted hydrocarbyl, and heterohydrocarbyl. Non-limiting examples of such atoms or groups are chloride, bromide, methyl, ethyl, propyl, butyl, octyl decyl, phenyl, benzyl, methoxide, ethoxide, isopropoxide, toxylate, triflate, formate, acetate, phenoxide and benzoate. It can be desirable when X is a halide or a $C_1$ to $C_{20}$ hydrocarbyl. In some embodiments it is desirable that X is chloride. The bridged catalyst component is generally made by contacting a bridge intermediate with a compound of the form $M(X)_2$. More details are provided in the Examples.

The present invention further includes a catalyst system comprising one or more of the above described bridged catalyst components and one or more activators and/or cocatalysts (as described in greater detail below) or the reaction product of an activator and/or cocatalyst, such as for example, methylaluminoxane (MAO) and optionally an alkylation/scavenging agent such as trialkylaluminum compound, for example triethylaluminum (TEAL). The above described metallocene catalyst components may also be supported as is known in the metallocene art. Typical supports may be a support such as talc, an inorganic oxide, clay, and clay minerals, ion-exchanged layered compounds, diatomaceous earth, silicates, zeolites or a resinous support material such as a polyolefin. Specific inorganic oxides include silica and alumina, used alone or in combination with other inorganic oxides such as magnesia, titania, zirconia and the like. Non-metallocene transition metal compounds, such as titanium tetrachloride, can also be incorporated into the supported catalyst component. The inorganic oxides used as support can be characterized as having an average particle size ranging from 30–600 microns, desirably from 30–100 microns, a surface area of 50–1,000 square meters per gram, desirably from 100–400 square meters per gram, and a pore volume of 0.5–3.5 cc/g, desirably from about 0.5–2 cc/g.

The bridged catalysts of the present invention may be used in combination with some form of activator in order to create an active catalyst system. The term "activator" is defined herein to be any compound or component, or combination of compounds or components, capable of enhancing the ability of one or more catalysts to polymerize olefins to polyolefins. Alklyalumoxanes such as methylalumoxane (MAO) are commonly used as metallocene activators. Generally alkylalumoxanes contain about 5 to 40 of the repeating units.

Alumoxane solutions, particularly methylalumoxane solutions, may be obtained from commercial vendors as solutions having various concentrations. There are a variety of methods for preparing alumoxane, non-limiting examples of which are described in U.S. Pat. Nos. 4,665,208, 4,952,540, 5,091,352, 5,206,199, 5,204,419, 4,874,734, 4,924,018, 4,908,463, 4,968,827, 5,308,815, 5,329,032, 5,248,801, 5,235,081, 5,103,031 and EP-A-0 561 476, EP 0 279 586, EP-A-0 594 218 and WO 94/10180, each fully incorporated herein by reference. (As used herein unless otherwise stated "solution" refers to any mixture including suspensions.)

Ionizing activators may also be used to activate the bridged catalysts. These activators are neutral or ionic, or are compounds such as tri(n-butyl)ammonium tetrakis (pentaflurophenyl)borate, which ionize the neutral catalyst compound. Such ionizing compounds may contain an active proton, or some other cation associated with, but not coordinated or only loosely coordinated to, the remaining ion of the ionizing compound. Combinations of activators may also be used, for example, alumoxane and ionizing activators in combinations, see for example, WO 94/07928.

Descriptions of ionic catalysts for coordination polymerization comprised of metallocene cations activated by non-coordinating anions appear in the early work in EP-A-0 277 003, EP-A-0 277 004 and U.S. Pat. Nos. 5,198,401 and WOA-92/00333 (incorporated herein by reference). These teach a desirable method of preparation wherein metallocenes (bisCp and monoCp) are protonated by an anion precursor such that an alkyl/hydride group is abstracted from a transition metal to make it both cationic and charge-balanced by the non-coordinating anion. Suitable ionic salts include, but are not limited to, tetrakis-substituted borate or aluminum salts having fluorided aryl-constituents such as phenyl, biphenyl and napthyl.

The term noncoordinating anion (NCA) means an anion that either does not coordinate to the cation or which is only weakly coordinated to the cation thereby remaining sufficiently labile to be displaced by a neutral Lewis base. Compatible noncoordinating anions are those that are not degraded to neutrality when the initially formed complex decomposes. Further, the anion will not transfer an anionic substituent or fragment to the cation so as to cause it to form a neutral four coordinate metallocene compound and a neutral by-product from the anion.

The use of ionizing ionic compounds not containing an active proton but capable of producing both the active metallocene cation and a noncoordinating anion is also known. See, for example, EP-A-0 426 637 and EP-A-0 573 403 (incorporated herein by reference). An additional method of making the ionic catalysts uses ionizing anion precursors which are initially neutral Lewis acids but form the cation and anion upon ionizing reaction with the metallocene compounds, for example the use of tris (pentafluorophenyl) borane, see EP-A-0 520 732 (incorporated herein by reference). Ionic catalysts for addition polymerization can also be prepared by oxidation of the metal centers of transition metal compounds by anion precursors containing metallic oxidizing groups along with the anion groups, see EP-A-0 495 375 (incorporated herein by reference).

Where the metal ligands include halogen moieties (for example, biscyclopentadienyl zirconium dichloride) which are not capable of ionizing abstraction under standard conditions, they can be converted via known alkylation reactions with organometallic compounds such as lithium or aluminum hydrides or alkyls, alkylalumoxanes, Grignard reagents, etc. See EP-A-O 500 944 and EP-A1-0 570 982 (incorporated herein by reference) for in situ processes describing the reaction of alkyl aluminum compounds with dihalo-substituted metallocene compounds prior to or with the addition of activating anionic compounds.

Desirable methods for supporting ionic catalysts comprising metallocene cations and NCA are described in U.S. Pat. Nos. 5,643,847; 6,143,686; and 6,228,795 (all fully incorporated herein by reference). These NCA support methods generally comprise using neutral anion precursors that are is sufficiently strong Lewis acids to react with the hydroxyl reactive functionalities present on the silica surface such that the Lewis acid becomes covalently bound.

Additionally, when the activator for the metallocene supported catalyst composition is a NCA, desirably the NCA is first added to the support composition followed by the addition of the bridged metallocene catalyst. When the activator is MAO, desirably the MAO and bridged metallocene catalyst are dissolved together in solution. The support is then contacted with the MAO/metallocene catalyst solution. Other methods and order of addition will be apparent to those skilled in the art.

The catalysts of the present invention can be used for the polymerization of α-olefins having at least two carbon atoms or the copolymerization of mixtures of α-olefins. For example, the present catalyst can be useful for catalyzing ethylene, propylene, butylene, pentene, hexene, 4-methylpentene and also for mixtures thereof. The catalysts of the present invention can be utilized for the polymerization of propylene to produce polypropylene, such as for example, high crystallinity polypropylene.

The polymerization and, where applicable, prepolymerization conditions are known in the art and need not be described in detail here. In general, polymerization is accomplished by contacting together either α-olefin monomer or a mixture of α-olefins in the presence of the above described catalyst system under polymerization conditions. The following examples are given as particular embodiments of the invention and to demonstrate the practice and advantages thereof.

EXAMPLES

These examples are provided merely to illustrate a few embodiments of the present invention, and are not intended to and do not limit the specification or scope of the claims. In these examples, all manipulations of air/moisture-sensitive materials were performed on a conventional vacuum/inert atmosphere line using standard Schlenk line techniques.

Example 1

The procedure as described in WO 99/12981 was utilized for synthesis of ligand intermediate A of the formula as shown below:

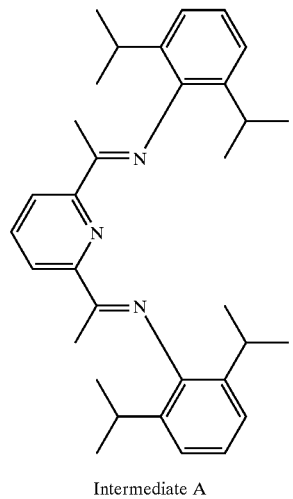

Intermediate A 2,6-diisopropylaniline (3.46 ml, 18.4 mmol) was added dropwise to a solution of 2,6-diacetylpyridine (1.5 g, 9.2 mmol) in absolute ethanol (25 ml) A few drops of glacial acetic acid was added and the solution was refluxed for 48 h. Concentration of the solution to half volume and cooling to 78° C. gave intermediate A as pale yellow crystals (80%). The calculated values for the intermediate C33H43N3 is: C, 82.3%; H, 8.9%; N, 8.7%. The observed results of the intermediate produced were: C, 81.9%; H, 8.5%; 8.7%. Fast atom bombardment mass spectrometry (FABMS) results are: M+(481). NMR analysis results are: 1H NMR (CDCl3): 8.6 B 7.9 [m, 3H, C5H3N], 7.2 B 6.9 [m, 6H, C6(CHMe2)H3], 2.73[sept, 4H, CHMe2], 2.26[s, 6H, C5H3N(CMeNAr)2] and 1.16[m, 24H, CHMe2].

Example 2

250 mg, 1.09 eq. of Intermediate A, and 95 mg of FeCl2.4H2O was weighed into a 10 ml Schlenk flask containing a stirbar. The flask was placed on a Schlenk manifold, backfilled 3 times with argon, and 10 ml of tetrahydrofurane (THF) were added while stirring. After 2 h, the THF was removed under vacuum. The resulting deep blue solid (formula below) was washed twice with ether and dried under vacuum.

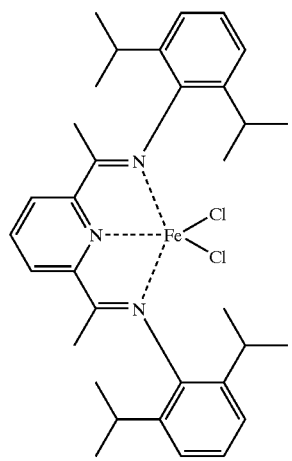

Example 3

This example shows creation of a ligand having C2/Class A symmetry. The same general synthesis is followed from Example 1, with the exception that the 2,6-diisopropylaniline is replaced with indene.

1-Amino-indene (18.4 mmol) was added to a solution of 2,6-diacetylpyridine (9.2 mmol) in absolute ethanol (50 ml). A few drops of glacial acetic acid was added and the solution is refluxed for 48 h. Concentration of the solution was reduced to half volume and the solution was cooled to room temperature and filtered to give the intermediate shown below.

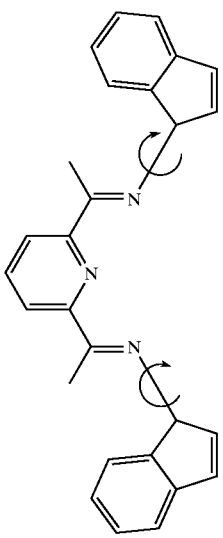

Intermediate B with symmetry $C_2/A$

Example 4

A catalyst from the ligand of Example 3 (Intermediate with symmetry C2/Class A) is synthesized by using the same general synthesis as in Example 2, to provide the catalyst component shown below.

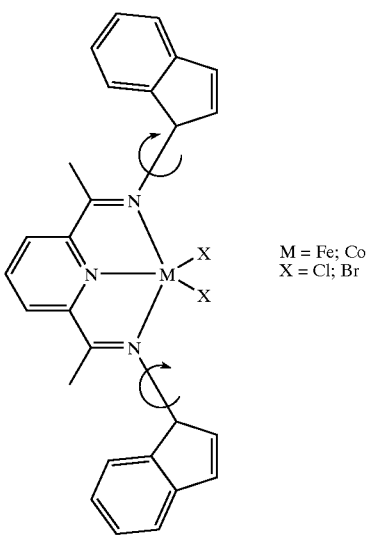

M = Fe; Co
X = Cl; Br

Catalyst with symmetry $C_2/A$

Example 5

This example shows creation of a ligand having C2/Class B symmetry. The first part of the synthesis for this ligand is different from that of Example 1 above. The first part of the synthesis starts with the reduction of the diacetylpyridine to a diamine by using the Leuckart-Wallach reaction. In scheme 1 below, a general reaction is shown for the reduction of a carbonyl to an amine.

Scheme 1. Reduction of a carbonyl compounds to amines (Leuckart-Wallach Reaction):

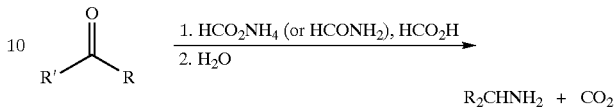

$R_2CHNH_2$ + $CO_2$

Example 6

This example illustrates the reduction of a carbonyl to an amine, specifically, the synthesis of 1-phenylethylamine (Vogel's Practical Organic Chemistry including qualitative organic analysis, 4$^{th}$ Ed, Furniss, B. S., et al., School of Chemistry Thames Polytechnic Longman Scientific and Technical, 1978). 126 g (2.0 mol) of ammonium formate, 72 g (0.6 mol) of acetophenone and a few chips of porous porcelain were added to a 250 ml flask fitted with a Claisen still-head carrying a short fractionating column; a thermometer expending nearly to the bottom of the flask was inserted, and a short condenser was set for downward distillation to the side arm. The flask was heated (either with a heating mantle or in an air batch); the mixture first melted to two layers and distillation occurs. The mixture became homogeneous at 150–155° C. and reaction took place with slight frothing. Heating was continued, until the temperature reached 185° C. (about 2 hours); acetophenone, water and ammonium carbonate distill. The heating was stopped at 185° C., the upper layer of acetophenone was separated from the distillate and returned without drying to the flask. The mixture was heated for 3 hours at 180–185° C. and allowed to cool; the acetophenone may be recovered from the distillate by extraction with 20 ml portions of toluene. The reaction mixture was transferred to a 250 ml separatory funnel and shaken with two 75 ml portions of water to remove formamide and ammonium formate. The crude (1-phenylethyl)formamide was transferred into the original reaction flask and the aqueous layer was extracted with two 20 ml portions of toluene. The toluene extracts were transferred to the flask, 75 ml of concentrated hydrochloric acid and a few chips of porous porcelain were added. The mixture was heated cautiously until about 40 ml of toluene was collected, and boiled gently under reflux for a further 40 minutes; hydrolysis proceeded rapidly to 1-phenylethylamine hydrochloride except for a small layer of unchanged acetophenone. The reaction mixture was allowed to cool, and the acetopenone was removed by extraction with four 20 ml portions of toluene. The aqueous acid solution was transferred to a 500 ml round-bottom flask equipped for steam distillation, a solution of 62.5 g of sodium hydroxide was cautiously added to 125 ml water, and steam distilled: the distillation flask was heated so that the volume remained nearly constant. Most of the amine was contained in the first 500 ml of distillate; the operation was stopped when the distillate was only faintly alkaline. The distillate was extracted with five 25 ml portions of toluene, the extract was dried with sodium hydroxide pellets and fractionally distilled. Toluene distilled over at 111° C., followed by the phylethylamine. The latter was collected as a fraction of b.p. 180–190° C. (the bulk of the product distilled at 184–186° C. (3); the yield was 43 g (59%).

Example 7

This example illustrates the synthesis of 2,6-(1,1'-diethylhydroxyimino)-pyridine (Dioxime) (Scheme 2). Hydroxylamine hydrochloride (0.98 g; 14.1 mmol) and pyridine (5 mL) were placed in a flask under Argon and equipped with a magnetic stirrer. 2,6-Diacetylpyridine (1,0 g; 6.1 mmol) was added and the mixture was refluxed for 8 h and stirred at room temperature for two days. The pyridine was removed under vacuum. Water (20 mL) was added to the residue. The white solid was washed with small amounts of water. The dioxime was dried overnight under vacuum to afford a white powder (1.08 g; 5.6 mmol; 92%), which was used without further purification. NMR analysis results are: $^1$H NMR (CD$_2$Cl$_2$), δ: 7.81 (d, 2H, Hmeta, J=7.8 Hz), 7.70 (t, 1H, Hpara, J=7.8 Hz), 2.79 (s, 2H, OH), 2.33 (s, 6H, Me).

Scheme 2 Synthesis of dioxime

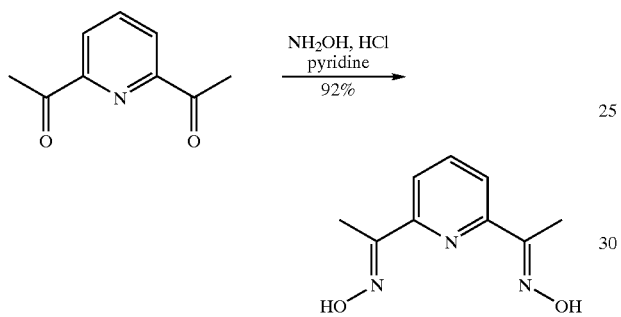

Example 8

The reduction of dioxime as obtained in Example 7 to the diamine is provided by using a following synthethic procedure (Scheme 3).

Synthesis of 2,6-(1,1'-diethylamino)-pyridine (Diamine). The 2,6-(1,1'-diethylhydroxyimino)-pyridine (500 mg; 2.6 mmol) was added in a flask placed under Argon and equipped with a magnetic stirrer and dissolved in ethanol (10 mL) and acetic acid (6 mL). Zinc powder (6 g; 94 mmol) was added dropwise over 10 minutes. After 1 h of stirring a white precipitate appeared. The mixture was stirred at room temperature for 24 h. The undissolved zinc was removed by filtration and washed with small amounts of ethanol. The filtrate was concentrated under vacuum. Small portions of water were added and evaporated to remove any remaining acetic acid. The mixture was made strongly basic (pH>12) by addition of saturated aqueous potassium hydroxide solution (around 56 mL) until all the Zn(OH)$_2$ was redissolved. The aqueous layer was transferred in a separatory funnel and extracted with four portions of diethyl ether (20 mL). The combined organic fractions were dried over MgSO$_4$ and the solvent was removed under vacuum to afford a colorless oil (310 mg; 1.87 mmol; 72%). NMR analysis results are: $^1$H NMR (CD$_2$Cl$_2$), δ: 7.59 (t, 1H, Hpara, J=7.8 Hz), 7.14 (d, 2H, Hmeta, J=7.8 Hz), 4.07 (q, 2H, CH, J=6.6 Hz), 1.79 (s, 4H, NH$_2$), 1.38 (d, 6H, Me, J=6.6 Hz).

Scheme 3. Synthesis of diamine

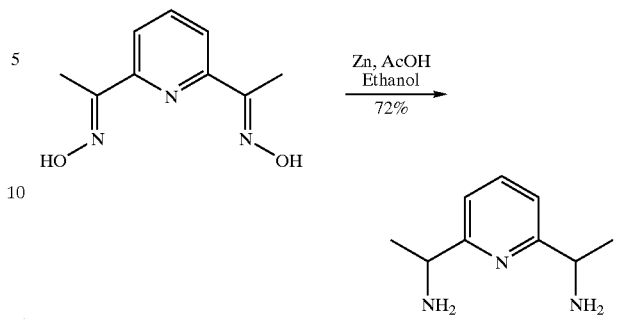

Example 9

This example provides a ligand for a catalyst with symmetry C2/Class B by reacting the diamine as obtained in Example 7 with a ketone (Scheme 4).

Scheme 4. Synthesis of a ligand for catalyst with symmetry C2/Class B

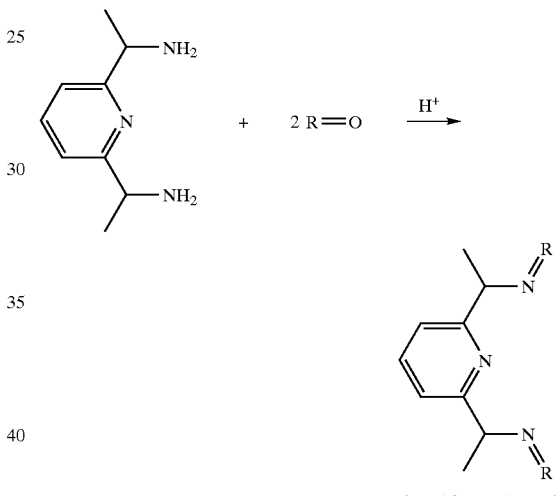

Ligand for catalyst with C$_2$/B symmetry

Example 10

This example illustrates the synthesis of bis-imine for a catalyst with C$_2$/class B symmetry based on the reaction of diamine with β-tetralone (Scheme 5).

In a 100 mL round bottom flask equipped with a stir bar, the diamine (0.50 g, 3.03 mmoles) and the β-tetralone (0.85 mL, 6.43 mmoles) were added to the flask at 25° C. the mixture produced a clear dark yellow liquid. The flask was then placed under vacuum and back-filled with argon three times and then left under argon. After stirring for 10 minutes, the mixture produced a pale yellow solid tar, which became very difficult to stir. 25 mL of ethanol was added to help stir the mixture. A clear orange-yellow solution was obtained. After stirring for 2 hours at 25° C., the solvent was removed under vacuum and obtained left a pale yellow foamy solid. $^1$H-NMR analysis showed that the product was mostly the desired bisimine ligand (78% yield). NMR analysis results are: $^1$H NMR (300 MHz, CD$_2$Cl$_2$, 35° C.) δ: 7.63 (t, 1H), 7.21 (d, 4H), 6.96 (t, 4H), 6.80 (t, 2H), 6.77 (m, 2H), 5.14 (d, 2H), 4.64 (d, 2H), 2.80 (t, 4H), 2.36 (t, 4H), 1.55 (d, 6H, Me).

Scheme 5. Synthesis of bis-imine by using β-tetralone

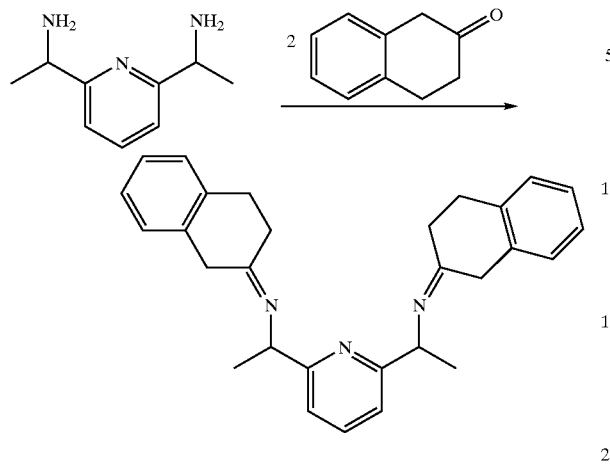

Example 11

This example illustrates the synthesis of bis-imine for a catalyst with $C_2$/class B symmetry based on the reaction of diamine with cyclohexanone (Scheme 6). The procedure as described in Example 9 was utilized for the synthesis of bis-imine.

Scheme 6. Synthesis of bis-imine by using cyclohexanone

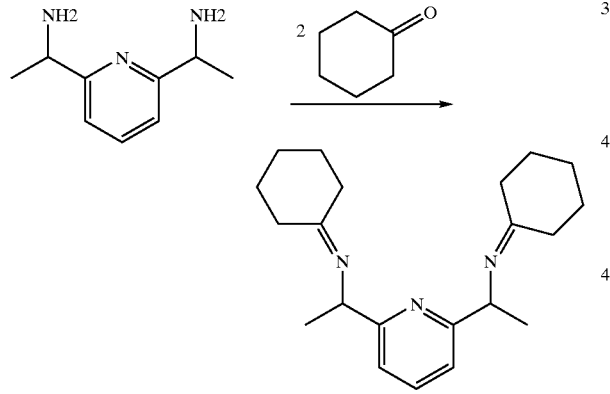

Example 12

This example illustrates the synthesis of bis-imine for a catalyst with $C_2$/class B symmetry, based on the reaction of diamine with mesitylaldehyde (Scheme 7). The procedure as described in Example 9 was utilized for synthesis of bis-imine. Bis-imine: NMR analysis results are: $^1$H NMR (300 MHz, $CD_2Cl_2$, 35° C.) δ: 8.7 (s, 2H, HCN), 7.66 (t, J=7.8 Hz, 1H, Hpara), (d, J=7.8 Hz, 2H, Hmeta), 6.88 (s, 4Hmeta, Mes), 4.63 (q, J=6.6 Hz, 2H, $HCH_3$,) 2.42 (s, 12H, $CH_3$ortho,Mes), 2.28 (s, 6H, $CH_3$para,Mes), 1.63 (d, J=6.6 Hz, 6H, Me).

Scheme 7. Synthesis of bis-imine by using mesitaldehyde

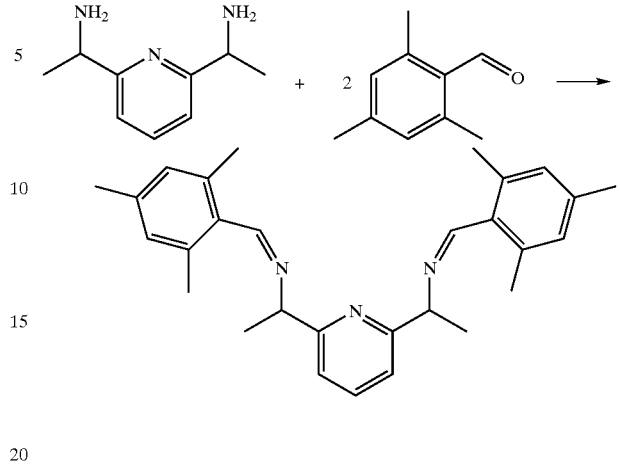

Example 13

Another catalyst synthesis procedure to produce a catalyst with symmetry C2/Class B is the same procedure as the one described in WO 98/30612 (with the exception of different R groups and position of double bonds in the structure), and is shown in the following reaction formula:

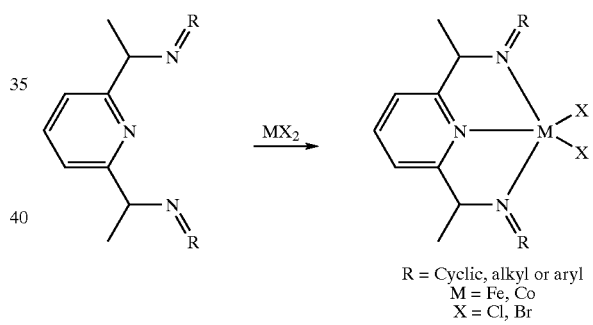

R = Cyclic, alkyl or aryl
M = Fe, Co
X = Cl, Br

The ligand (1.05 eq.) of Example 9 and the metal salt in its hydrated or anhydrous form are added together in a Schlenk flask under inert atmosphere and then charged with THF. The mixture is stirred for several hours or until no detectable unreacted salts are observed. The mixture is filtered in air and the solids are washed with Et2O and dried under vacuum.

Example 14

To synthesize a ligand for catalyst with a Cs/Class B symmetry or with a C1/Class B symmetry, a similar procedure as the one used for the C2/Class B symmetry is used. The exception is that only two different ketones are reacted with diamine. The general procedure for this synthesis is shown in the formula below (Scheme 8).

Scheme 8. Synthesis of a ligand for catalyst with Cs/type B symmetry

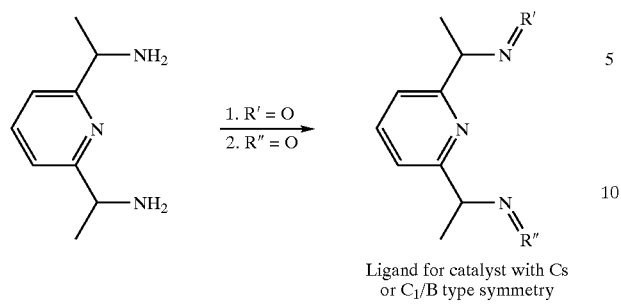

Ligand for catalyst with Cs or C₁/B type symmetry

Example 15

To synthesize a structure with a C2/Class C symmetry, a similar procedure as the one used for the C2/Class B symmetry is used. The exception is that only one acetyl group is reduced on the 2,6-diacetylanaline. The general procedure for this synthesis is shown in the formula below where only one of the acetyls is reduced to the amine.

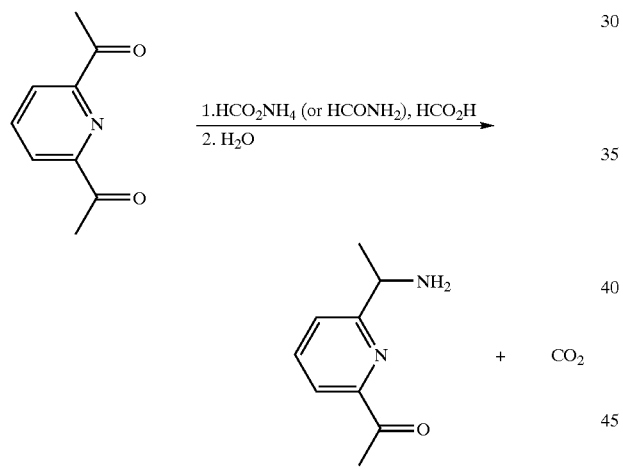

Example 16

In this example, the amine of Example 14 is reacted with a ketone to provide the R group double bond to the nitrogen.

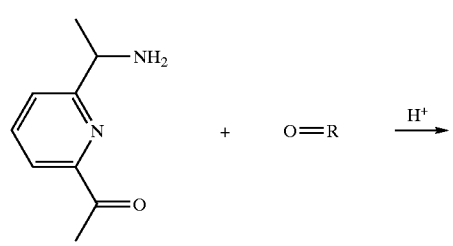

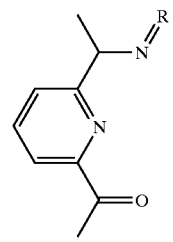

Example 17

In this Example, an amine is reacted with the mono-acetyl intermediate of Example 15 to provide the R group with a single bond to the nitrogen as shown in the formula below.

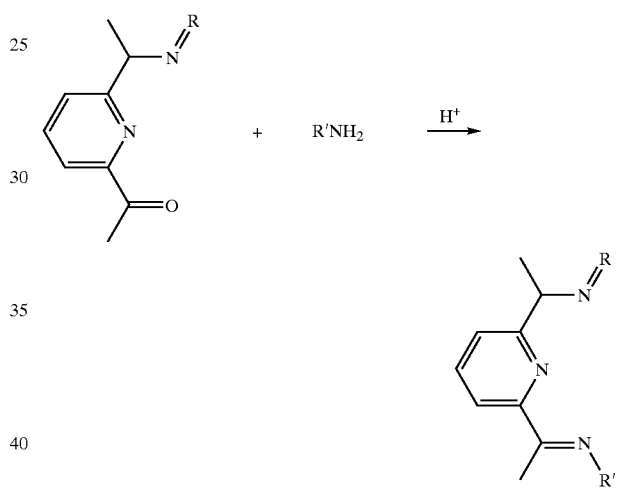

Example 18

A catalyst is then synthesized according to the procedure described in Example 13.

Simply by using different R groups bonded to the nitrogen atoms with a single bond, a double bond, or with one single bond and one double bond, the symmetries for $C_1$ and $C_S$ may also be obtained. Some examples for the different symmetries are summarized in Table 1 for the structure as shown in Table 1.

Any patents, patent applications, articles, books, treatises, and any other publications cited herein, are hereby incorporated by reference for all that they teach or suggest.

TABLE 1

Examples of Symmetries

M = Fe; C
X = Cl; Br

| Symmetry | R1 | R2 |
|---|---|---|
| C2/Class A | indanyl | indanyl |
| C2/Class B | indenyl | indenyl |
| C2/Class C | indanyl | indenyl |
| Cs/Class A | cyclopentadienyl-methyl | fluorenyl |
| Cs/Class B | cyclopentadienylidene | fluorenylidene |
| Cs/Class C | cyclopentadienyl-methyl | fluorenylidene |
| Cs/Class D | cyclopentadienylidene | fluorenyl |
| C1/Class A | t-butyl-cyclopentadienyl-methyl | fluorenyl |

TABLE 1-continued

Examples of Symmetries

M = Fe; C
X = Cl; Br

| Symmetry | R1 | R2 |
|---|---|---|
| C1/Class B | t-butyl-cyclopentadienylidene | fluorenylidene |
| C1/Class C | t-butyl-cyclopentadienyl-methyl | fluorenylidene |
| C1/Class D | t-butyl-cyclopentadienylidene | fluorenyl |

X-Ray Data of $C_2$ Symmetric Iron Complexes

The solid-state structures of iron complexes have been determined by X-ray diffraction method of single crystals. The selected crystallographic data are summarized in Table 2 and structures are depicted in the formulas from Example 4 and as shown below the table.

TABLE 2

Selected lengths and angles of $C_2$ symmetric iron complexes:

| Length (Å) or Angle (deg) of Bonds | Complex 1 | Complex 2 |
|---|---|---|
| Fe—N(imine) | 2.177; 2.228 | 2.222; 2.227 |
| Fe—N(pyridine) | 2.100 | 2.103 |
| N(imine)—C(L) | 1.453; 1.474 | 1.430; 1.439 |
| N(imine)—Fe—N(imine) | 146.6 | 146.8 |
| Fe—N(imine)—C(L) | 117.9; 123.6 | 122.4; 121.7 |
| C—N(imine)—C(L) | 119.6; 123.1 | 120.3; 121.1 |

Complex 1: 2,6-[bis-1-(1-indanylimino)ethyl]pyridine iron (II) chloride
Complex 2: 2,6-bis[1-(1-naphthylimino)ethyl]pyridine iron dichloride
* Complex 1 and 2 have the formulas shown above:

2,6-[bis-1-(1-indanylimino)ethyl]pyridine iron (II) chloride (Complex 1) has the structure shown in the formula below:

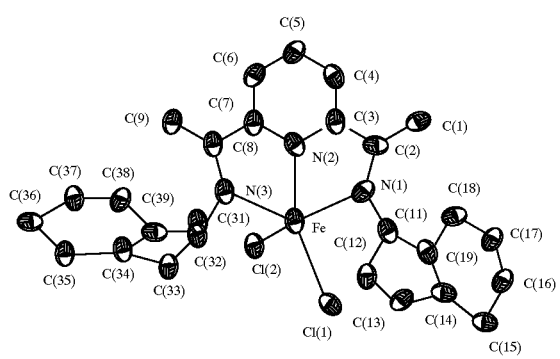

2,6-bis[1-(1-naphthylimino)ethyl]pyridine iron dichloride (Complex 2): has the structure shown in the formula below:

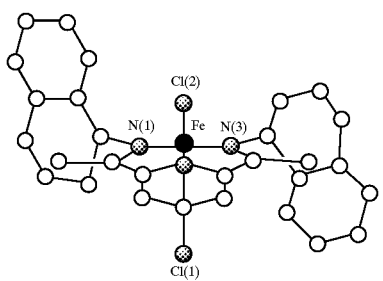

While the illustrative embodiments of the invention have been described with particularity, it will be understood that various other modifications will be apparent to and can be readily made by those skilled in the art without departing from the scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which this invention pertains.

What is claimed is:

1. A catalyst system comprising the formula:

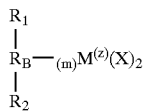

wherein M is a 3d, 4d or 5d transition metal; each X is an atom or group bonded to M and are the same or different; $R_1$ and $R_2$ are the same or different and are substituted or unsubstituted cyclopentadienyl groups; $R_B$ is a structural bridge between $R_1$ and $R_2$ comprising three heteroatoms bonded to M, with each of $R_1$ and $R_2$ bonded to the same or different heteroatom of $R_B$ which heteroatom is also bonded to M; Z is the coordination number of M and is greater than or equal to 4; m is the number of bonds between M and heteroatoms of $R_B$ and m≥2; and with $R_1$, $R_2$ and $R_B$ selected to provide $C_1$, $C_2$ or $C_S$ symmetry.

2. The system of claim 1, wherein the heteroatoms are selected from the group consisting of O, N, S and P.

3. The system of claim 1, wherein $R_1$ is bonded to one of the heteroatoms, and $R_2$ is bonded to a different one of the heteroatoms.

4. The system of claim 1, wherein M is selected from the group consisting essentially of Fe, Co and Ni.

5. The system of claim 1, wherein M is Fe, and wherein $R_1$ is bonded to one of the three heteroatoms, and $R_2$ is bonded to a heteroatom different than the heteroatom to which $R_1$ is bonded; M is Fe, Co or Ni.

6. The system of claim 5, wherein each X is independently selected from the group consisting of halides and substituted or unsubstituted hydrocarbons.

7. A method of making a catalyst system comprising contacting an activator with a bridged compound having the formula:

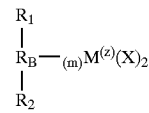

wherein M is a 3d, 4d or 5d transition metal; each X is an atom or group bonded to M and are the same or different; $R_1$ and $R_2$ are the same or different and are substituted or unsubstituted cyclopentadienyl groups; $R_B$ is a structural bridge between $R_1$ and $R_2$ and comprises three heteroatoms bonded to M, with each of $R_1$ and $R_2$ bonded to the same or different heteroatom of $R_B$ which heteroatom is also bonded to M; Z is the coordination number of M and is greater than or equal to 4; m is the number of bonds between M and heteroatoms of $R_B$ and m≥2; and $R_1$, $R_2$ and $R_B$ are selected to provide a bridged compound with $C_1$, $C_2$ or $C_S$ symmetry.

8. A catalyst system comprising the formula:

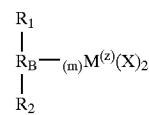

wherein M is a 3d, 4d or 5d transition metal; each X is an atom or group bonded to M and is the same or different; $R_1$, and $R_2$ are the same or different and are substituted or unsubstituted cyclopentadienyl groups; $R_B$ is a structural bridge between $R_1$ and $R_2$ comprising three heteroatoms-bonded to M, with each of $R_1$ and $R_2$ bonded to the same or different heteroatom of $R_B$ which heteroatom is also bonded to M; Z is the coordination number of M and is greater than or equal to 4; and m is the number of bonds between M and the heteroatoms of $R_B$ and is greater than or equal to 2.

* * * * *